United States Patent [19]

Foglio et al.

[11] 4,331,677
[45] May 25, 1982

[54] 7-OXO-4-1-AZA-BICYCLO-[3,2,0]-HEPTANE DERIVATIVES

[75] Inventors: Maurizio Foglio; Giovanni Franceschi; Cosimo Scarafile; Federico Arcamone, all of Milan, Italy

[73] Assignee: Farmitalia Carlo Erba S.p.A., Milan, Italy

[21] Appl. No.: 95,790

[22] Filed: Nov. 19, 1979

[30] Foreign Application Priority Data

Nov. 24, 1978 [GB] United Kingdom ............... 45966/78

[51] Int. Cl.$^3$ .................. C07D 499/00; A61K 31/425
[52] U.S. Cl. .............................. 424/270; 260/245.2 R
[58] Field of Search ....................... 260/245.2; 424/270

[56] References Cited

U.S. PATENT DOCUMENTS

| | | | |
|---|---|---|---|
| 4,076,826 | 2/1977 | Christensen et al. | 424/270 |
| 4,110,165 | 8/1978 | Cole et al. | 260/245.3 |
| 4,123,539 | 10/1978 | DiNinno | 424/270 |
| 4,155,912 | 5/1979 | Menard et al. | 424/270 |
| 4,168,314 | 9/1979 | Christensen et al. | 424/270 |
| 4,182,711 | 1/1980 | Ueda | 548/178 |
| 4,187,228 | 2/1980 | Luk | 260/245.3 |
| 4,189,493 | 2/1980 | Christensen et al. | 544/327 |
| 4,207,323 | 6/1980 | Beattie et al. | 260/245.3 |
| 4,215,124 | 7/1980 | Christensen et al. | 424/275 |
| 4,244,965 | 1/1981 | Howarth | 260/245.3 |

Primary Examiner—Nicholas S. Rizzo
Attorney, Agent, or Firm—Stevens, Davis, Miller & Mosher

[57] ABSTRACT

This invention relates to 7-oxo-4-thia-1-aza-bicyclo-[3,2,0]-heptane derivatives, to processes for their synthesis from esters of penicillanic acid 1-oxide, and to intermediate compounds obtained in the synthesis.

More particularly, the present invention relates to new and novel compounds of formula (1):

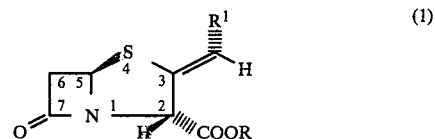

wherein

R is a hydrogen atom, an alkyl having from 1 to 5 carbon atoms, trichloroethyl, benzyl, p-nitrobenzyl, diphenylmethyl, acetoxymethyl, pivaloyloxymethyl, phthalidyl, trimethylsilyl or a group of formula

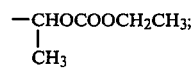

and $R^1$ is $-CH_2OH$, $-CH_2OCOR^2$, $-CH_2OR^3$, $-COOR^2$, $-CHO$, $-CH_2SH$, $-CH_2SR^4$, $-CH_2NH_2$, $-CH_2NHCOR^2$ in which $R^2$ is an alkyl having from 1 to 5 carbon atoms, aryl, aralkyl or a five- or six-membered heterocyclic ring containing one or more heteroatoms; $R^3$ is an alkyl having from 1 to 5 carbon atoms, benzyl, trityl, trialkylsilyl; and $R^4$ is a five- or six-membered heterocyclic ring containing one or more heteroatoms, benzyl, trityl or trialkylsilyl; and to the synthesis of such compounds.

Compounds of formula (1) (E+Z isomers) are endowed with antibacterial activity.

4 Claims, No Drawings

4,331,677

7-OXO-4-1-AZA-BICYCLO-[3,2,0]-HEPTANE DERIVATIVES

This invention relates to 7-oxo-4-thia-1-aza-bicyclo-[3,2,0]-heptane derivatives, to processes for their synthesis from esters of penicillanic acid 1-oxide, and to intermediate compounds obtained in the synthesis.

More particularly, the present invention relates to new and novel compounds of formula (1):

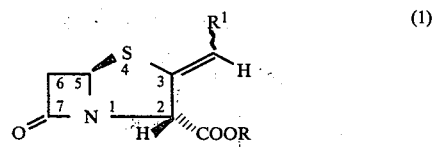

wherein

R is a hydrogen atom, an alkyl having from 1 to 5 carbon atoms, trichloroethyl, benzyl, p-nitrobenzyl, diphenylmethyl, acetoxymethyl, pivaloyloxymethyl, phthalidyl, trimethylsilyl or a group of formula

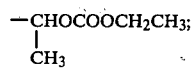

and $R^1$ is —$CH_2OH$, —$CH_2OCOR^2$, —$CH_2OR^3$, —$COOR^2$, —CHO, —$CH_2SH$, —$CH_2SR^4$, —$CH_2NH_2$, —$CH_2NHCOR^2$ in which $R^2$ is an alkyl having from 1 to 5 carbon atoms, aryl, aralkyl or a five- or six-membered heterocyclic ring containing one or more heteroatoms; $R^3$ is an alkyl having from 1 to 5 carbon atoms, benzyl, trityl, trialkylsilyl; and $R^4$ is a five- or six-membered heterocyclic ring containing one or more heteroatoms, benzyl, trityl or trialkylsilyl; and to the synthesis of such compounds.

Pharmaceutically acceptable salts of compounds of formula (1) are also included within the scope of the present invention.

Compounds of formula (1) (E+Z isomers), related to clavulanic acid (T. T. Howarth, A. G. Brown: J. Chem. Soc. Chem. Comm. 266, 1976), are endowed with antibacterial activity and are useful as therapeutic agents in the treatment of infectious diseases. For such purpose, they may be administered either parenterally or orally, as acids, pharmaceutically acceptable salts, and esters.

Compounds of formula (1) are prepared by means of processes described in the reaction scheme set out below.

In the compounds illustrated in this reaction scheme, $R_6$ represents a lower alkyl, trichloroethyl, benzyl, p-nitrobenzyl diphenyl-methyl, acetoxymethyl, pivaloyloxymethyl, phthalidyl, or trimethylsilyl group, or a group of the formula —$CH(CH_3)OCOOC_2H_5$; $R_1$ represents a group of the formula —$CH_2OCOR_2$, —$CH_2OR_3$, —$COOR_2$, —$CH_2NHCOR_2$ or —$CH_2SR_4$ wherein $R_2$ represents a lower alkyl, aryl, aralkyl, or heterocyclic group, $R_3$ represents a lower alkyl, benzyl, trialkylsilyl or trityl group, and $R_4$ represents a five- or six-membered heterocyclic ring containing one or more heteroatoms or a benzyl, trityl or trialkylsilyl group; $R^5$ represents an alkyl (preferably lower alkyl), aryl, aralkyl or heterocyclic group; and X represents an electron withdrawing group, for example one of the formula —$COOR_2$, —CN or —$CONH_2$, or a hydrogen atom $R_2$ being as above defined.

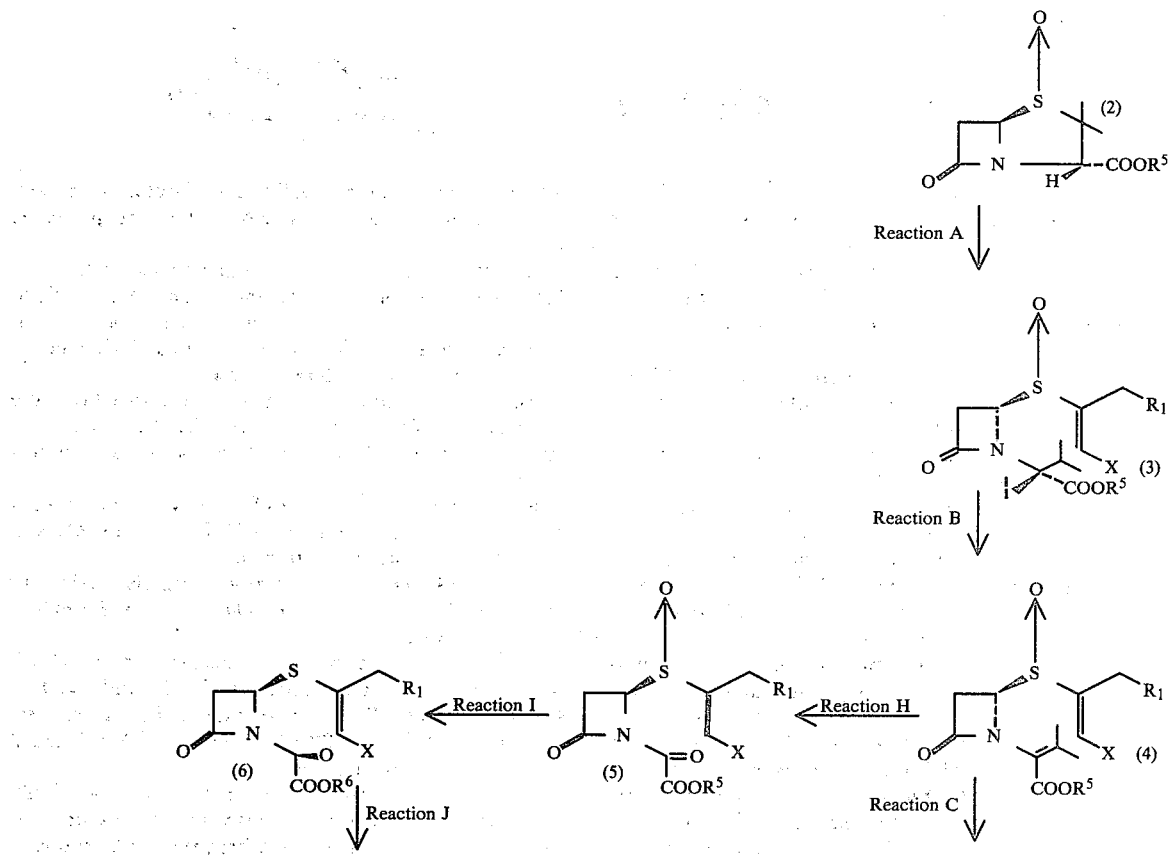

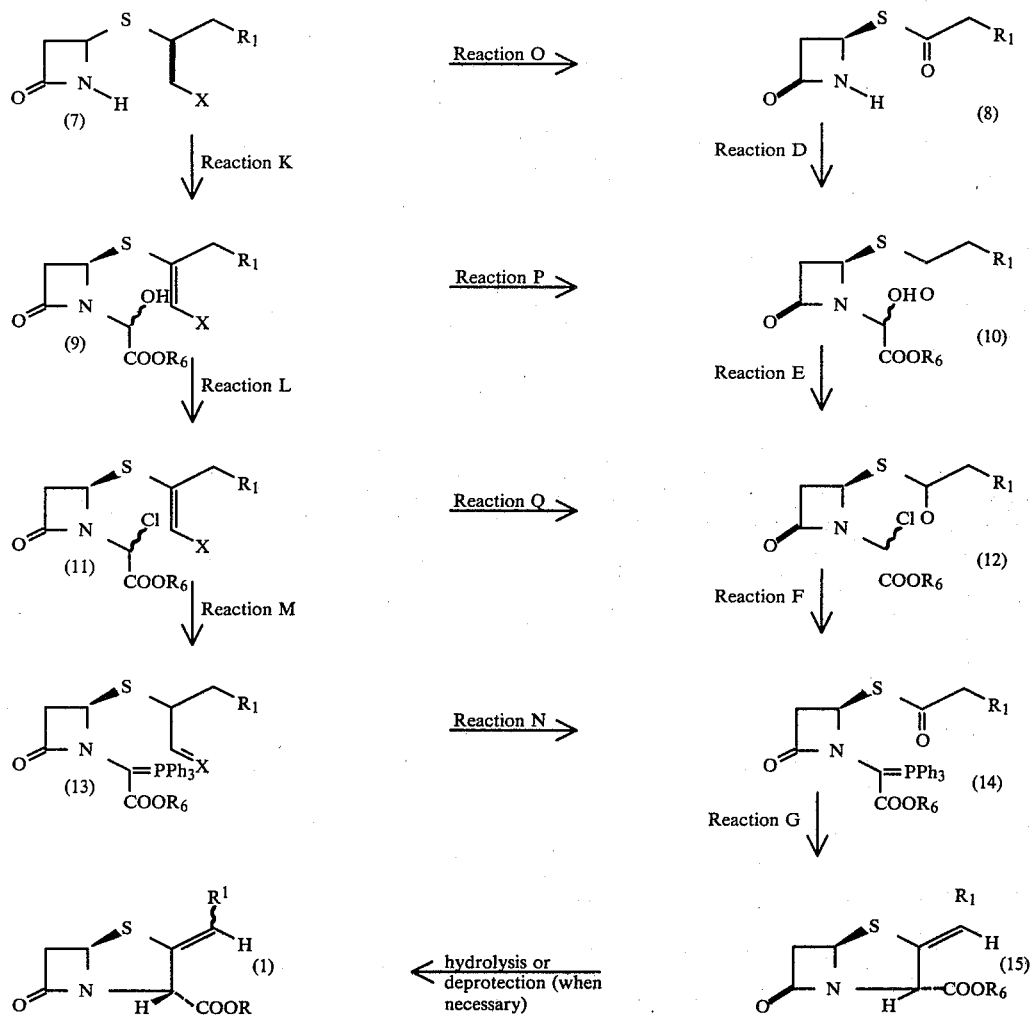

Reaction A comprises reacting compound (2) with an allenic compound of the formula $CHX=C=CHR_1$, or with an acetylenic compound of the formula $CX\equiv C-CH_2R_1$, X and $R_1$ being as above defined, by heating to from 50° C. to 120° C. in an inert solvent. Suitable inert solvents are benzene, toluene, and dimethylformamide.

Reaction B comprises an isomerization effected in an inert solvent at room temperature. Dichloromethane is suitable as the inert solvent.

Reaction C comprises three reactions in succession: reduction of the sulphoxide bond of compound (4), ozonolysis of both double bonds, and hydrolysis.

Reaction D comprises condensing compound (8) with a glyoxylic acid ester of the formula $CHO.COOR_6$, wherein $R_6$ is as above defined, at a temperature of from 40° C. to 100° C. Compound (10) is obtained as a mixture of its diastereoisomers.

Reaction E is a chlorination reaction. Suitable conditions for this are the use of thionyl chloride as chlorinating agent in the presence of a base such as pyridine at a temperature of from −20° C. to +20° C. Compound (12) is obtained as a mixture of its diastereoisomers.

Reaction F comprises a condensation between compound (12) and triphenylphosphine carried out at a temperature not exceeding 50° C. and in the presence of a base. The reaction is usually carried out at room temperature, and pyridine and 2,6-lutidine are preferred bases.

Reaction G is a ring closure effected simply by heating compound (14) at a temperature of from 20° C. to 140° C. in an inert solvent such as toluene, benzene, or ethyl acetate and in the presence of a catalytic amount of an organic base, preferably pyridine.

Reaction H comprises an ozonolysis carried out at a temperature of from <30° C. to −78° C. in a solvent such as dichloromethane, ethyl acetate, or tetrahydrofuran.

Reaction I is a reduction effected with phosphorus tribromide, preferably at from 0° C. to −40° C., and preferably in dimethylformamide.

Reaction J comprises a hydrolysis, usually carried out in methanol in the presence of silica gel or under mildly basic conditions.

Reaction K comprises condensing compound (7) with a glyoxylic acid ester of the formula $CHO.COOR_6$, wherein $R_6$ is as above defined, at a temperature of from 40° C. to 100° C. Compound (9) is obtained as a mixture of its diastereoisomers.

Reaction L is a chlorination reaction. Suitable conditions for this are the use of thionyl chloride as chlorinating agent, in the presence of a base such as pyridine at a temperature of from −20° C. to +20° C. Compound (11) is obtained as a mixture of its diastereoisomers.

Reaction M is carried out under the same conditions as reaction F above, except that the temperature is from 40° C. to 80° C.

Reaction N is an ozonolysis reaction carried out with the carbon-phosphorus double bond protected by protonation with a strong acid such as trifluoroacetic acid, deprotonation being effected at the end of the ozone treatment using sodium bicarbonate. The reaction temperature is desirably from −20° C. to −78° C.

Reactions O, P and Q are ozonolysis reactions carried out under the same conditions as reaction H above.

Compounds (1) in which R is a hydrogen atom and $R^1$ is —CH$_2$OH, —CH$_2$SH, or —CHO are obtained simply by removal of the various protecting groups $R_2$, $R_3$ and $R_4$, by reduction of the group —COOR$_2$ or hydrolysis of the group —COOR$_6$.

The invention is illustrated by the following examples:

EXAMPLE 1

4β-Vinylthio-[1-carbomethoxymethyl-2-methoxycarbonyl]-1-[1-methoxycarbonyl-2-methyl-2-propenyl]-azetidin-2-one-S-oxide.

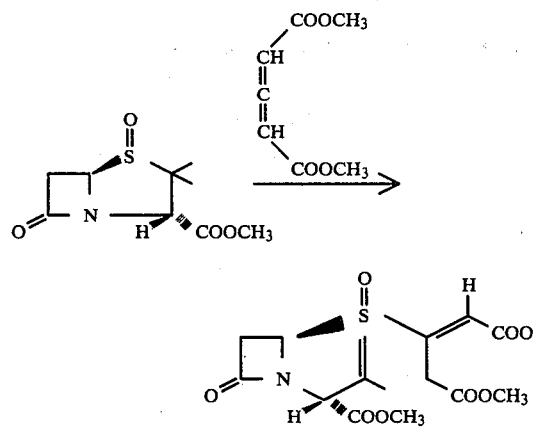

1.5 g of methylpenicillinate 1-oxide were dissolved in 30 ml of toluene. To the solution, 2.2 g of glutinic acid dimethyl ester were added and the resulting solution was treated at refluxing temperature for 4 hours. The very main product can be purified by column chromatography using benzene-ethyl acetate to give 1.8 g of 4β-vinylthio-[1-carbomethoxymethyl-2-methoxycarbonyl]-1-[1-methoxycarbonyl-2-methyl-2-propenyl]-azetidin-2-one-S-oxide.

I.R. (CHCl$_3$), $\nu_{max}$: 1770, 1740 cm$^{-1}$,

P.M.R. (CDCl$_3$) δ: 2.00 (s, CH$_3$—C(=O)—),
2.93 (dd, J = 14.0 and 5.0 Hz, α C(3)H),
3.40 (dd, J = 14.0 and 2.0 Hz, β C(3)H),
3.88 (s, three CH$_3$O)
5.00 (br.s, N—CH(COOC(H$_3$))—C(=)< and one of the vinylidene protons), 5.24 (br.s, C(4)H and one of the vinylidene protons),

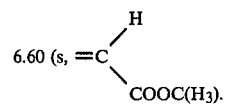
6.60 (s, =CH—COOC(H$_3$)).

EXAMPLE 2

4β-Vinylthio-[1-carbomethoxymethyl-2-methoxycarbonyl]-1-[1-methoxycarbonyl-2-methyl-1-propenyl]-azetidin-2-one-S-oxide

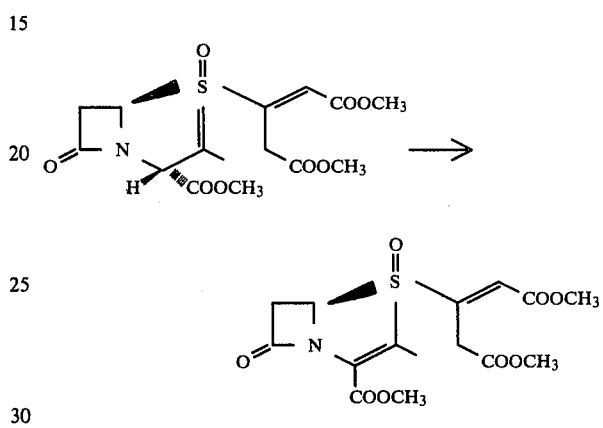

2.8 g of 4β-vinylthio-[1-carbomethoxymethyl-2-methoxycarbonyl]-1-[1-methoxycarbonyl-2-methyl-2-propenyl]-azetidin-2-one-S-oxide were dissolved in 50 ml of dichloromethane and 0.5 ml of triethylamine were added. The solution was left at room temperature for one night and then evaporated in vacuo twice from carbon tetrachloride. The residue consisted of pure 4β-vinylthio-[1-carbomethoxymethyl-2-methoxycarbonyl]-1-[methoxycarbonyl-2-methyl-1-propenyl]-azetidin-2-one-S-oxide in quantitative yields.

| | |
|---|---|
| I.R. (CHCl$_3$), $\nu_{max}$: | 1775, 1725,cm$^{-1}$ |
| P.M.R. (CDCl$_3$) δ: | 2.12 and 2.30 (two s, (CH$_3$)$_2$C=), |
| | 3.78 (s, three CH$_3$O), |
| | 5.11 (br.s, C(4)H), |
| | 6.64 (s, =C—H). |

EXAMPLE 3

4β-Vinylthio-[1-carbomethoxymethyl-2-methyoxycarbonyl]-1-methoxyoxaloyl-azetidin-2-one-S-oxide

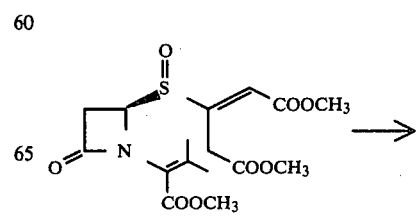

-continued

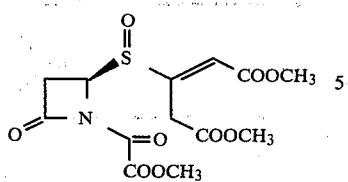

1.8 g of 4β-vinylthio-[1-carbomethoxymethyl-2-methoxycarbonyl]-1-[1-methoxycarbonyl-2-methyl-1-propenyl]azetidin-2-one-S-oxide were dissolved in 100 ml of methylene chloride and cooled at −78° C. A flow of ozone in oxygen was bubbled through this solution until a blue color appeared. The resulting ozonide was reduced by shaking with an aqueous solution of Na₂S₂O₅. The organic phase was dried over Na₂SO₄ and evaporated in vacuo, to give 1.4 g of 4β-vinylthio-[1-carbomethoxymethyl-2-methoxycarbonyl]-1-methoxyoxaloyl-azetidin-2-one-S-oxide.

| | |
|---|---|
| I.R. (CHCl₃), ν_max: | 1830, 1720 cm⁻¹, |
| P.M.R. (CDCl₃) δ: | 3.70 (s, two CH₃O), |
| | 3.88 (s, CH₃O), |
| | 5.27 (dd, J = 5.5 and 2.5 Hz, C(4)H), |
| | 6.65 (s, =C—H). |

EXAMPLE 4

4β-Vinylthio-[1-carbomethoxymethyl-2-methoxycarbonyl]-1-methoxyoxaloyl-azetidin-2-one

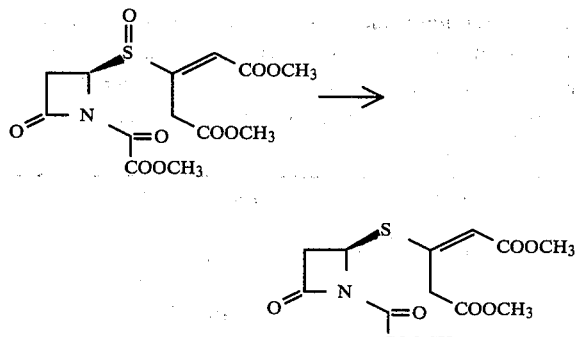

A solution of 1.5 g of 4β-vinylthio-[1-carbomethoxymethyl-2-methoxycarbonyl]-1-methoxyoxaloyl-azetidin-2-one-S-oxide in 10 ml of anhydrous dimethylformamide was cooled at −20° C. and 0.6 ml of phosphorous tribromide were added under stirring. After 10 minutes, the mixture was poured in ethyl acetate and washed twice with water. The organic layer was dried over Na₂SO₄ and evaporated in vacuo to give 1.1 g of 4β-vinylthio-[carbomethoxymethyl-2-methoxycarbonyl]-1-methoxyoxaloyl-azetidin-2-one.

P.M.R. (CDCl₃): 3.76 δ(s, two CH₃O), 3.97 δ(s, CH₃O), 5.65 δ(dd, J=5.5 and 2.5 Hz, C(4)H), 6.20 δ(s, =C—H).

EXAMPLE 5

4β-Vinylthio-[1-carbomethoxymethyl-2-methoxycarbonyl]-azetidin-2-one.

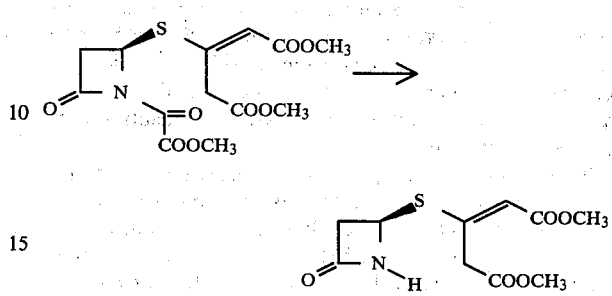

A solution of 1.6 g of 4β-vinylthio-[1-carbomethoxymethyl-2-methoxycarbonyl]-1-methoxyoxaloyl-azetidin-2-one in 50 ml of methanol was left overnight under vigorous stirring together with 5 g of silica gel. After filtering the insoluble material, the methanolic solution was evaporated and the residue chromatographed on silica gel, eluting with benzene-ethylacetate, to give 0.8 g of 4β-vinylthio-[1-carbomethoxymethyl-2-methoxycarbonyl]-azetidin-2-one.

I.R. (CHCl₃), ν_max: 1780, 1740, 1715 cm⁻¹
P.M.R. (CDCl₃) δ: 3.70 (s, two CH₃O), 3.83 (s,—CH₂—C=C), 5.11 (br.s, C(4)H), 5.77 (s,=C—H).

EXAMPLE 6

4β-Methoxycarbonylacetylthio-azetidin-2-one

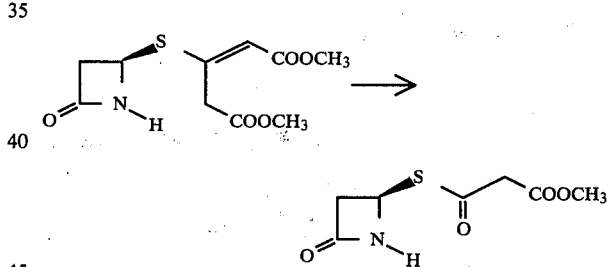

A solution of 0.250 g of 4β-vinylthio-[1-carbomethoxymethyl-2-methoxy-carbonyl]-azetidin-2-one in 30 ml of dichloromethane was cooled at −78° C. and a flow of ozone in oxygen was bubbled through this solution until a blue color appeared. The mixture was shaken with an aqueous solution of Na₂S₂O₅ and dried over Na₂SO₄. Obtained: 0.150 g of 4β-methoxycarbonylacetylthio-azetidin-2-one.

P.M.R. (CDCl₃): 3.67 δ(s, CO-CH₂-COOC(H₃), 3.81 δ(s, CH₃O), 5.35 δ(br.s, C(4)H).

EXAMPLE 7

4β-Vinylthio-[1-carbomethoxymethyl-2-methoxycarbonyl]-1-[1-methoxycarbonyl-1-hydroxymethyl]-azetidin-2-one

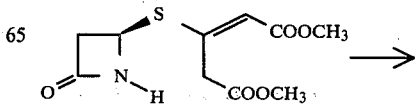

-continued

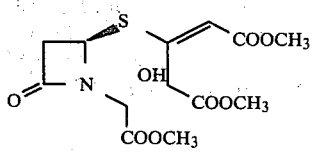

1.8 ml of methyl glyoxylate (freshly prepared from ozonolysis of dimethyl fumarate) were dissolved in 50 ml of benzene and the solution was refluxed for 30 minutes through a Dean-Stark apparatus. After cooling at 50° C., 0.8 g of 4β-vinylthio-[1-carbomethoxymethyl-2-methoxycarbonyl]-azetidin-2-one were added and the resulting solution refluxed again at boiling temperature for 3 hours. After a short column chromatography on silica gel for the purification of the product from the excess of methyl glyoxylate, 1.7 g of 4β-vinylthio-[1-carbomethoxymethyl-2-methoxycarbonyl]-1-[methoxycarbonyl-1-hydroxymethyl]-azetidin-2-one were obtained, as a mixture of diastereoisomers.

P.M.R. (CDCl₃): 3.75, 3.90 and 3.95 δ (three s, three CH₃O),
5.38 δ (s, N—CH—O(H),
           |
           COO
5.40 δ. (br.s, C(4)H),
6.00 δ (s, =C—H).

EXAMPLE 8

4β-Methoxycarbonylacetylthio-1-[1-methoxycarbonyl-1-hydroxymethyl]-azetidin-2-one

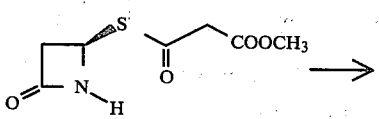

A solution of 0.450 g of freshly prepared methyl glyoxylate in 30 ml of benzene was boiled through a Dean-Stark apparatus for 30 minutes. 0.200 g of 4β-methoxycarbonylacetylthio-azetidin-2-one were added and the mixture was maintained at boiling temperature for 3 hours. After a short column chromatography for the purification from the excess of methyl glyoxylate, 0.110 g of 4β-methoxycarbonylacetylthio-1-[1-methoxycarbonyl-1-hydroxymethyl]-azetidin-2-one were obtained.

P.M.R. (CDCl₃): 3.76 δ (s, CO—CH₂—COOC(H₃)),
3.90 and 3.94 δ (two s, two CH₃O),
5.60 δ (s, N    O(H)
            \  /
             C
            / \
           H   COOC(H₃)
5.72 δ (br.s, C(4)H).

EXAMPLE 9

4β-Vinylthio-[1-carbomethyoxymethyl-2-methoxycarbonyl]-1-[1-methoxycarbonyl-1-chloromethyl]-azetidin-2-one

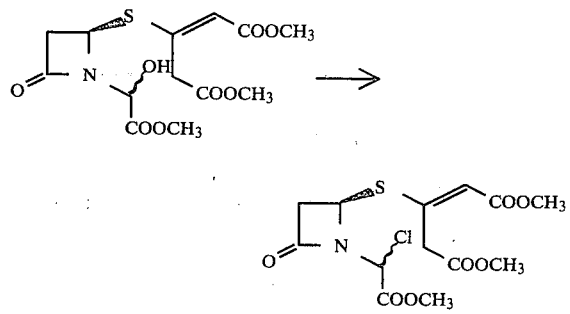

To a solution of 0.200 g of 4β-methoxycarbonylacetylthio-1-[1-methoxycarbonyl-1-hydroxymethyl]-azetidin-2-one in 3 ml of anhydrous tetrahydrofuran cooled at 0° C., 0.047 ml of pyridine and 0.042 ml of thionyl chloride were added under stirring. The mixture was left stirring for 30 minutes, the insoluble material (pyridine hydrochloride) was filtered off and the resulting solution was evaporated in vacuo at 30° C. The residue was 0.180 g of 4β-vinylthio-[1-carboxymethoxymethyl-2-methoxycarbonyl]-1-[1-methoxycarbonyl-1-chloromethyl]-azetidin-2-one as a mixture of diastereoisomers.

I.R. (CHCl₃), $\nu_{max}$: 1780, 1745, 1715 cm⁻¹,
P.M.R. (CDCl₃) δ: 3.74, 3.75 and 3.92 (three s, three CH₃O), 5.30 (br.s, C(4)H), 5.91 (s, CHCl), 6.10 (s, =C—H).

EXAMPLE 10

4β-Methoxycarbonylacetylthio-1-[1-methoxycarbonyl-1-chloromethyl]-azetidin-2-one

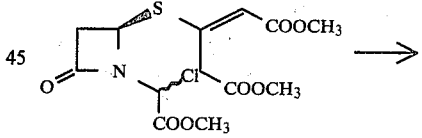

A solution of 0.150 g of 4β-vinylthio-[1-carbomethoxymethyl-2-methoxycarbonyl]-1-[1-methoxycarbonyl-1-chloromethyl]-azetidin-2-one in 10 ml of dichloromethane was cooled at −78° C. and a flow of ozone in oxygen was bubbled therethrough until a blue color appeared. The mixture was then shaken with an aqueous solution of Na₂S₂O₅ and, after drying over Na₂SO₄, evaporated in vacuo to give 0.090 g of 4β-methoxycarbonylacetylthio-1-(1-methoxycarbonyl-1-chloromethyl]-azetidin-2-one.

I.R. (CHCl₃), $\nu_{max}$: 1785, 1750 cm⁻¹,

-continued

P.M.R. (CDCl₃) δ :

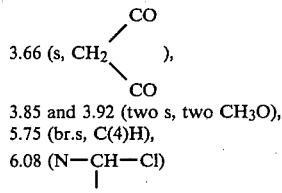

3.66 (s, CH₂), 3.85 and 3.92 (two s, two CH₃O),
5.75 (br.s, C(4)H),
6.08 (N—CH—Cl)

EXAMPLE 11

4β-Methoxycarbonylacetylthio-1-[1-methoxycarbonyl-1-triphenylphosphoranylidenemethyl]-azetidin-2-one A solution of 0.210 g of 4β-methoxycarbonylacetylthio-1-[1-methoxycarbonyl-1-chloromethyl]-azetidin-2-one in 8 ml of anhydrous tetrahydrofuran, containing 0.038 ml of pyridine and 0.250 g of triphenylphosphine was left overnight at room temperature after a gentle heating. The phosphorane, 4β-methoxycarbonylacetylthio-1-[1-methoxycarbonyl-1-triphenylphosphoranylidenemethyl]-azetidin-2-one, was purified on silica gel. Obtained: 0.120 g.

I.R. (CHCl₃), ν$_{max}$: 1755 (large) cm⁻¹,
P.M.R. (CDCl₃) δ: 3.60 and 3.74 (two, CH₃O), 5.80 (br.s,C(4)H), 7.1–8.1 (m, 3 C₆H₅ groups).

EXAMPLE 12

4β-Vinylthio-[1-carbomethoxymethyl-2-methoxycarbonyl]-1-[1-methoxycarbonyl-1-triphenylphosphoranylidenemethyl]-azetidin-2-one A solution of 0.200 g of 4β-vinylthio-[1-carbomethoxymethyl-2-methoxycarbonyl]-1-[1-methoxycarbonyl-1-chloromethyl]-azetidin-2-one in 4 ml of tetrahydrofuran and 4 ml of dioxane, containing 0.047 ml of pyridine and 0.300 g of triphenylphosphine, was heated at 65° C. for 4 hours. The resulting compound 4β-vinylthio-[1-carbomethoxymethyl-2-methoxycarbonyl]-1-[1-methoxycarbonyl-1-triphenylphosphoranylidenemethyl]-azetidin-2-one was purified on silica gel. Obtained: 0.220 g.

I.R. (CHCl₃), ν$_{max}$: 1755 (large), 1715 cm⁻¹,
P.M.R. (CDCl₃)δ: 3.65 and 3.72 (two s, two CH₃O), 5.45 (br.s, C(4)H), 6.68 (s, =C—H), 7.2–8.0 (m, 3 C₆H₅ groups).

EXAMPLE 13

4β-Methoxycarbonylacetylthio-1-[1-methoxycarbonyl-1-triphenylphosphoranylidenemethyl]-azetidin-2-one A solution of 0.100 g of 4β-vinylthio-[1-carbomethoxymethyl-2-methoxycarbonyl]-1-[1-methoxycarbonyl-1-triphenylphosphoranylidenemethyl]-azetidin-2-one in 6 ml of dichloromethane was cooled at −20° C., and 7 ml of 10% solution of trifluoroacetic acid in dichloromethane were added. A flow of ozone in oxygen was bubbled therethrough for one minute, the solution degassed with nitrogen, and 0.2 ml of trimethyphosphite were added. The resulting solution was shaken with a saturated solution of NaHCO₃ and dried over Na₂SO₄, to give 0.060 g of 4β-methoxycarbonylacetylthio-1-[1-methoxycarbonyl-1-triphenylphosphoranylidenemethyl]-azetidin-2-one.

I.R. (CHCl₃), ν$_{max}$: 1755 (large) cm⁻¹.

EXAMPLE 14

Methyl-(2R,5R)-E-3-methoxycarbonylmethylene-7-oxo-4-thia-1-azabicyclo-[3,2,0]heptane-2-carboxylate (E + Z)

0.080 g of 4β-methoxycarbonylacetylthio-1-[1-methoxycarbonyl-1-triphenyl-phosphoranylidenemethyl]-azetidin-2-one were dissolved in 3 ml of toluene and heated at 120° C. for 30 minutes. The cyclized product methyl-(2R,5R)-E-3-methoxycarbonylmethylene-7-oxo-4-thia-1-azabicyclo-[3,2,0]heptane-2-carboxylate was purified from triphenyl phosphine oxide by short column chromatography. Obtained: 0.036 g as a mixture of E+Z isomers. Purification of the very major component (E isomer) was made by TLC.

E Isomer

I.R. (CHCl₃), $\nu_{max}$: 1792, 1750, 1700 cm⁻¹,

P.M.R. (CDCl₃)δ: 3.31 (dd, J=16.5 and 4.0 Hz, αC(6)H), 3.86 (dd, J=16.5 and 2.0 Hz, βC(6)H), 3.91 and 3.92 (two s, two CH₃O), 5.53 (dd, J=4.0 and 2.0 Hz, C(5)H), 5.64 (d, J=1.0 Hz, C(2)H), 6.29 (d, J=1.0 Hz, =C—H).

M.S.: m/e 257, 0355 (M⁺, calc. for C₁₀H₁₁NO₅S 257, 0358); m/e 215, 0253 (M—CH₂CO, calc. for C₈H₉NO₄S 215, 0252); m/e 156, 0119 (M—CH₂CO—COOCH₃, calc. for C₆H₆NO₂S 156, 0119)

EXAMPLE 15

4β-Vinylthio-[1-carbomethoxymethyl-2-methoxycarbonyl]-1-[1-methoxycarbonyl-2-methyl-1-propenyl]-azetidin-2-one

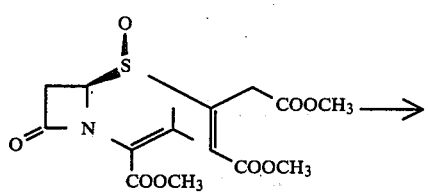

1.3 g of 4β-vinylthio-[1-carbomethoxymethyl-2-methoxycarbonyl]-1-[1-methoxycarbonyl-2-methyl-1-propenyl]-azetidin-2-one-S-oxide were dissolved in 20 ml of anhydrous dimethylformamide and cooled at −20° C.; 0.5 ml of phosphorous tribromide were added and the mixture left under stirring and cooling for 30 minutes. Ethyl acetate was added and the organic phase washed twice with water and dried over Na₂SO₄. After evaporation in vacuo, 1.0 g of the title compound were obtained.

PMR (CDCl₃):

2.03 (s, 3 H, N\\__/Me )

2.26 (s, 3 H, N\\__/Me )

3.32 (m, J = 3 Hz, 5 Hz, 2 H, H-3)
3.70–3.80 (11 H, CH₂COOCH₃,

=CH—COOCH₃, C(=O)/ \\COOCH₃ )

5.50 (dd, J = 3 Hz, 5 Hz, 1 H, H-4)
5.97 (s, 1 H, =CH)

EXAMPLE 16

4β-Methoxycarbonylacetylthio-1-methoxyoxaloyl-azetidin-2-one

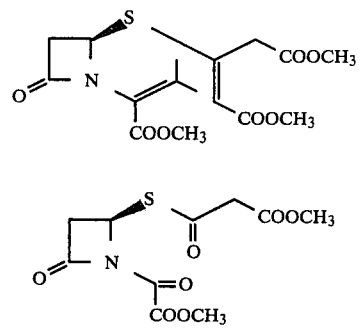

A solution of 0.450 g of 4β-vinylthio-[1-carbomethoxymethyl-2-methoxycarbonyl]-1-[1-methoxycarbonyl-2-methyl-1-propenyl]-azetidin-2-one in 50 ml of dichloromethane was cooled at −78° C., and a flow of ozone in oxygen was bubbled therethrough until a blue color appeared. The oxonide was reduced by shaking the organic phase with a solution of Na₂S₂O₅. After drying over Na₂SO₄ and evaporating in vacuo 0.280 g of the title compound were obtained.

| P.M.R. (CDCl₃) δ: | 3.08 (dd, J = 4 Hz, 14 Hz, 1 H, H(3)α) |
|---|---|
| | 3.55 (dd, J = 5 Hz, 14 Hz, 1 H, H(3)β) |
| | 3.70 (s, 2 H, CH₂COOCH₃) |
| | 3.80 (s, 3 H, CH₃COOCH₃) |
| | 3.97 (s, 3 H, COCOOCH₃) |
| | 5.82 (dd, J = 5 Hz, 4 Hz, 1 H, C(4)H). |

EXAMPLE 17

4β-Methoxycarbonylacetylthio-azetidin-2-one

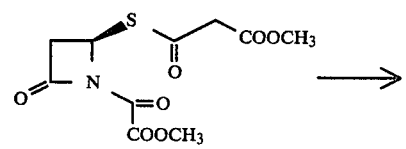

To a solution of 0.380 g of 4β-methoxycarbonylacetylthio-1-methoxy-oxaloyl-azetidin-2-one in 50 ml of methanol, 2 g of silica gel were added and the resulting mixture was left under stirring for 60 minutes. After filtering the insoluble material, the residue consisted of 0.210 g of the title compound. P.M.R. (CDCl₃): identical to spectrum of Example 6.

EXAMPLE 18

Benzyl-(2R,5R)-E-3-methoxycarbonylmethylene-7-oxo-4-thia-1-azabicyclo-[3,2,0]-heptane-2-carboxylate

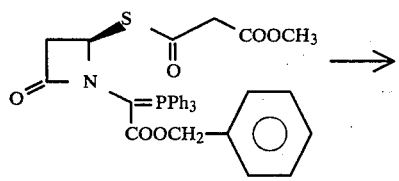

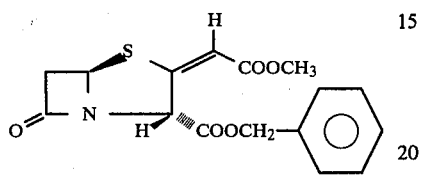

0.120 g of 4β-methoxycarbonylacetylthio-1-[1-benzyloxycarbonyl-1-triphenylphosphoranylidenemethyl]-azetidin-2-one were dissolved in 4 ml of toluene and heated for 60 minutes at 100° C. The resulting title compound was purified from POPh3 by short column chromatography to give 0.040 g of the pure compound.

| P.M.R. (CDCl$_3$)δ: | 3.22 (dd, J = 2 Hz, 16 Hz, 1 H, H-6 β) |
|---|---|
| | 3.74 (dd, J = 4 Hz, 16 Hz, 1 H, H-6 α) |
| | 3.77 (s, 3 H, CH$_3$OCO) |
| | 5.18 (s, 2 H, CH$_2$Ph) |
| | 5.36 (dd, J = 4 Hz, 2 Hz, 1 H H-5) |
| | 5.51 (d, J = 1.5 Hz, 1 H, H-2) |
| | 6.12 (d, J = 1.5 Hz, 1 H, = CH) |
| | 7.33 (m, 5 H, Ph) |

What is claimed is:

1. A compound of the formula

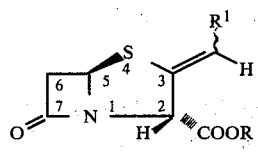

wherein

R is a hydrogen atom, an alkyl having from 1 to 5 carbon atoms, trichloroethyl, benzyl, p-nitrobenzyl, diphenylmethyl, acetoxymethyl, pivaloyloxymethyl, phthalidyl, trimethylsilyl, or a group of formula

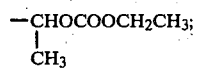

$R^1$ is —CH$_2$OH, —CH$_2$OCOR$^2$, —COOR$^2$, —CHO, —CH$_2$SH, —CH$_2$SR$^4$, —CH$_2$NH$_2$, —CH$_2$NH-COR$^2$ in which R$^2$ is an alkyl having from 1 to 5 carbon atoms, and $R^4$ is benzyl, trityl or trialkylsilyl.

2. A compound of formula

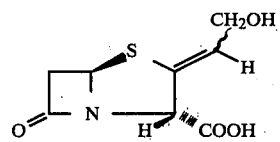

3. A pharmaceutical composition comprising an effective amount of an antibiotic compound as defined in claim 1, or a pharmaceutically acceptable salt thereof, in admixture with a pharmaceutically acceptable diluent or carrier.

4. The treatment of infectious diseases, said treatment comprising administering to a host in need of such treatment, a therapeutically effective amount of a compound as defined in claim 1 or of a pharmaceutically acceptable salt thereof.

* * * * *

UNITED STATES PATENT AND TRADEMARK OFFICE
CERTIFICATE OF CORRECTION

PATENT NO. : 4,331,677
DATED : May 25, 1982
INVENTOR(S) : Maurizio FOGLIO, et al.

It is certified that error appears in the above-identified patent and that said Letters Patent is hereby corrected as shown below:

In the abstract please change formula 1 to read as follows:

-- 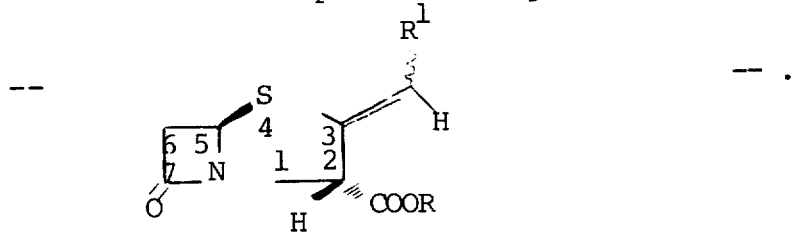 -- .

Column 1, formula 6 should be

-- 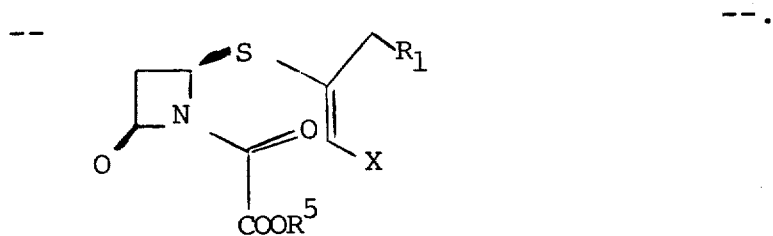 -- .

UNITED STATES PATENT AND TRADEMARK OFFICE
CERTIFICATE OF CORRECTION

PATENT NO. : 4,331,677

DATED : May 25, 1982

INVENTOR(S) : Maurizio FOGLIO, et al.

Page 2 of 8

It is certified that error appears in the above-identified patent and that said Letters Patent is hereby corrected as shown below:

Column 2, formula 3 should read:

-- 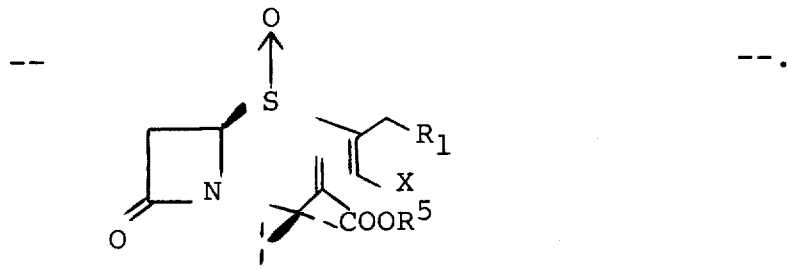 --.

Column 2, formula 4 should read:

-- 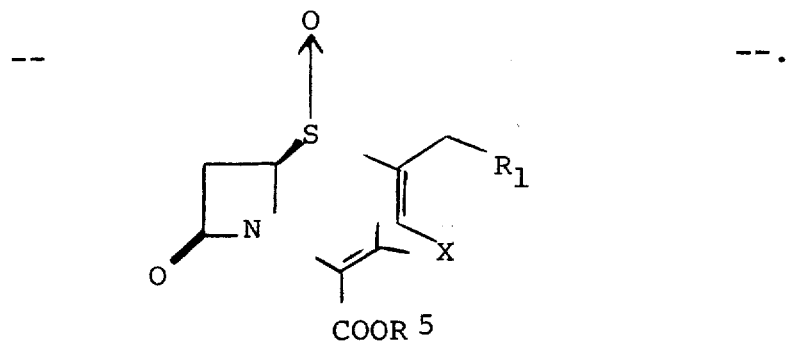 --.

UNITED STATES PATENT AND TRADEMARK OFFICE
CERTIFICATE OF CORRECTION

PATENT NO. : 4,331,677

DATED : May 25, 1982

INVENTOR(S) : Maurizio FOGLIO, et al.

It is certified that error appears in the above-identified patent and that said Letters Patent is hereby corrected as shown below:

Column 3, formula 13 should read:

-- 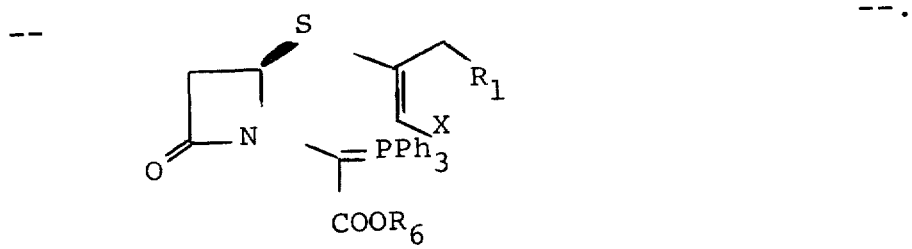 --.

Column 4 formula 10 should read:

-- 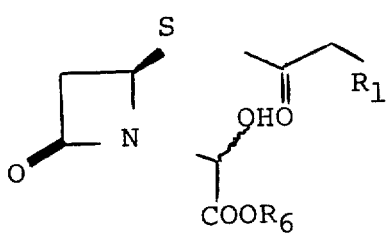 --.

UNITED STATES PATENT AND TRADEMARK OFFICE
CERTIFICATE OF CORRECTION

PATENT NO. : 4,331,677

DATED : May 25, 1982

INVENTOR(S) : Maurizio FOGLIO, et al.

It is certified that error appears in the above-identified patent and that said Letters Patent is hereby corrected as shown below:

Column 4, formula 12 should read:

-- 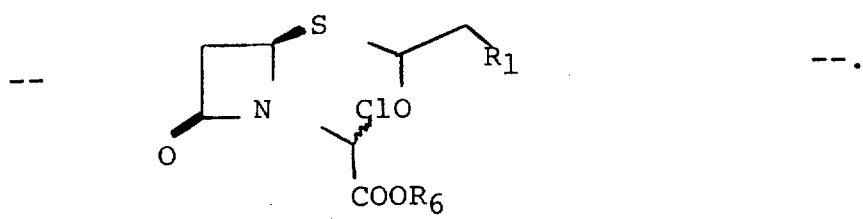 --.

Column 4, formula 15 should read:

-- 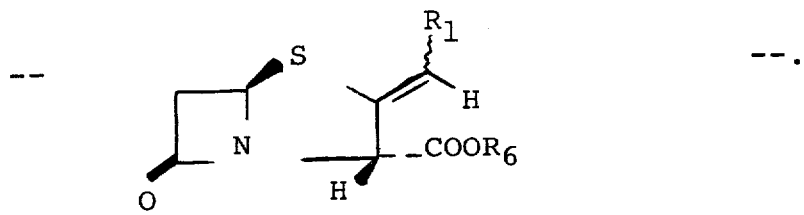 --.

UNITED STATES PATENT AND TRADEMARK OFFICE
CERTIFICATE OF CORRECTION

PATENT NO. : 4,331,677

DATED : May 25, 1982

INVENTOR(S) : Maurizio FOGLIO, et al.

It is certified that error appears in the above-identified patent and that said Letters Patent is hereby corrected as shown below:

Column 5, formula opposite line 40 should read:

-- 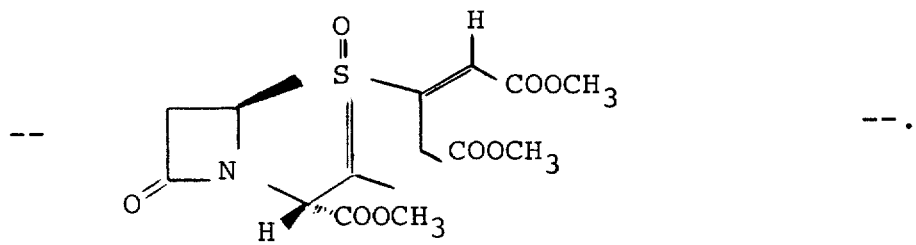 --.

Column 6, formula opposite line 20 should read:

-- 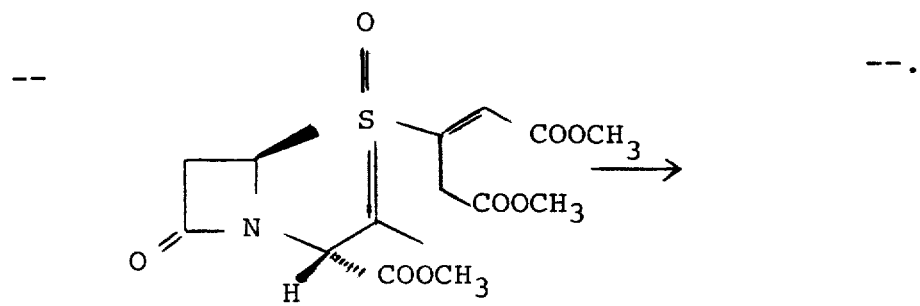 --.

UNITED STATES PATENT AND TRADEMARK OFFICE
CERTIFICATE OF CORRECTION

PATENT NO. : 4,331,677

DATED : May 25, 1982

INVENTOR(S) : Maurizio FOGLIO, et al.

It is certified that error appears in the above-identified patent and that said Letters Patent is hereby corrected as shown below:

Column 6, formula opposite line 25 should read:

-- 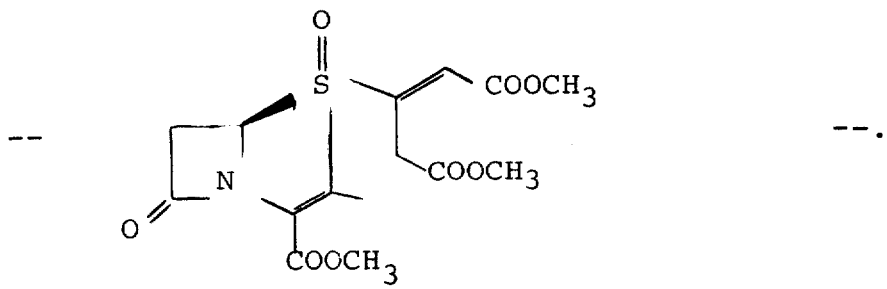 --.

Column 9, formula opposite line 5 should read:

-- 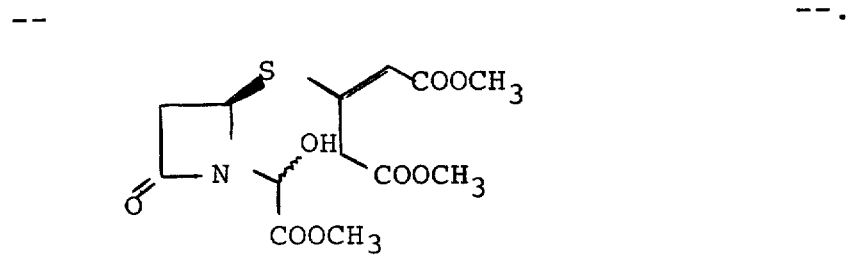 --.

UNITED STATES PATENT AND TRADEMARK OFFICE
CERTIFICATE OF CORRECTION

PATENT NO. : 4,331,677
DATED : May 25, 1982
INVENTOR(S) : Maurizio FOGLIO, et al.

It is certified that error appears in the above-identified patent and that said Letters Patent is hereby corrected as shown below:

Column 9, formula opposite line 45 should read:

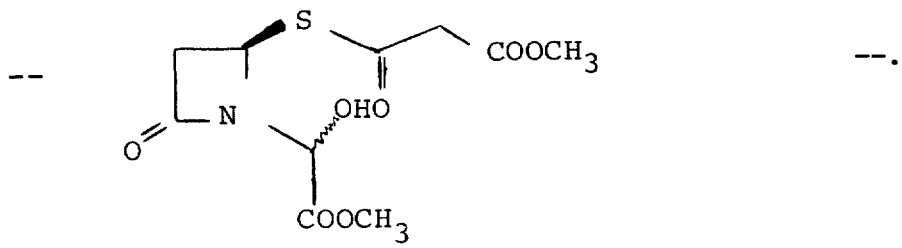

Column 12, formula opposite line 55 should read:

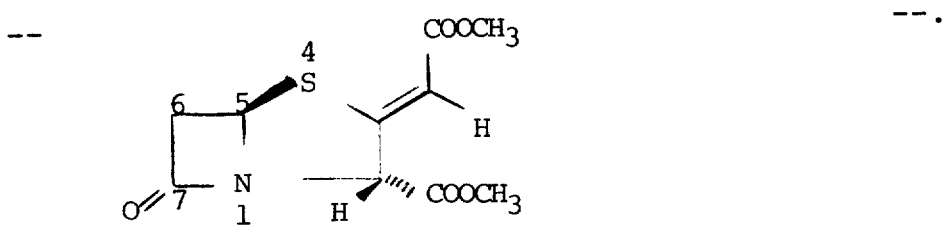

UNITED STATES PATENT AND TRADEMARK OFFICE
CERTIFICATE OF CORRECTION

PATENT NO.  : 4,331,677
DATED       : May 25, 1982
INVENTOR(S) : Maurizio FOGLIO, et al.

It is certified that error appears in the above-identified patent and that said Letters Patent is hereby corrected as shown below:

Column 13, formula opposite line 30 should read:

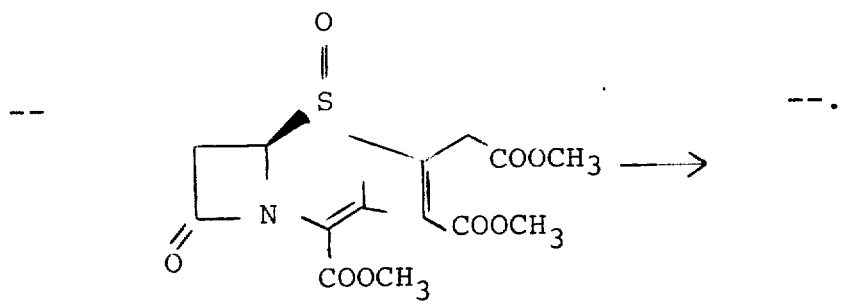

Signed and Sealed this

Nineteenth Day of March 1985

[SEAL]

Attest:

DONALD J. QUIGG

Attesting Officer          Acting Commissioner of Patents and Trademarks